United States Patent
Fisher et al.

(10) Patent No.: US 6,641,994 B2
(45) Date of Patent: *Nov. 4, 2003

(54) METHODS OF IDENTIFYING ANTI-VIRAL AGENTS

(75) Inventors: Christopher Fisher, Kalamazoo, MI (US); Wanxia He, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/728,466

(22) Filed: Dec. 1, 2000

(65) Prior Publication Data

US 2001/0029022 A1 Oct. 11, 2001

Related U.S. Application Data

(60) Division of application No. 09/648,215, filed on Aug. 25, 2000, now abandoned, which is a continuation-in-part of application No. 09/382,616, filed on Aug. 25, 1999, now Pat. No. 6,200,746.

(51) Int. Cl.$^7$ .............................. C12Q 1/70; C12Q 1/48; C12Q 1/18

(52) U.S. Cl. ................................ 435/5; 435/15; 435/32
(58) Field of Search ................................ 435/5, 15, 32; 514/1

(56) References Cited

U.S. PATENT DOCUMENTS

| | | |
|---|---|---|
| 5,283,173 A | 2/1994 | Fields et al. |
| 5,376,742 A | 12/1994 | Krause |
| 5,457,189 A | 10/1995 | Crooke et al. |
| 5,547,846 A | 8/1996 | Bartsch et al. |
| 5,576,206 A | 11/1996 | Schlegel |
| 5,625,031 A | 4/1997 | Webster et al. |
| 5,629,161 A | 5/1997 | Müller et al. |
| 5,681,944 A | 10/1997 | Crooke et al. |
| 5,736,318 A | 4/1998 | Münger et al. |
| 5,811,232 A | 9/1998 | Crooke et al. |

FOREIGN PATENT DOCUMENTS

| | | | |
|---|---|---|---|
| EP | 0666270 | * | 8/1995 |
| WO | 92/20652 | | 8/1995 |
| WO | 98/13502 | | 4/1998 |

OTHER PUBLICATIONS

Ben–Bassat et al. Cancer Research 57(17):3741–3750 (1997).*

Antinore, et al., "The human papillomavirus type 16 E7 gene product interacts with and *trans*–activates the AP1 family of transcription factors," *EMBO. J.*, 15:1950–60 (1996).

Arroyo, et al., "Association of the Human Papillomavirus Type 16 E7 Protein with S–Phase–Specific E2F–Cyclin A Complex," *Mol. Cel. Biol.* 13:6537–6456 (1993).

Banks, et al., "Ability of the HPV16 E7 protein to bind RB and induce DNA synthesis is not sufficient for efficient transforming activity in NIH3T3 cells," *Oncogene* 5:1383–1389 (1990).

Cane et al., "Harnessing the Biosynthetic Code: Combinations, Permutations, and Mutations," *Science* 282:63–68 (1998).

Chen, et al., "Cyclin–Binding Motifs Are Essentials for the Function of p21$^{CIP1}$," *Mol. Cell. Biol.* 16:4673–82 (1996).

Cheng, et al., "Differentiation–dependent up–regulations of the human papillomavirus E7 gene reactivities cellular DNA replication in suprabasal differentiated keratinocytes," *Genes & Dev.* 9:2335–49 (1995).

Chow, et al., "Papillomavirus DNA Replication," *Intervirology* 37:150–8 (1994).

Ciccolini, et al., "Functional studies of E7 proteins from different HPV types," *Oncogene* 9:2633–8 (1994).

Colas, et al., "The impact of two–hybrid and related methods on biotechnology," *TIBTECH* 16:355–363 (1998).

Connell–Crowley, et al., "Phosphorylation Independent Activation of Human Cyclin–Dependent Kinase 2 by Cyclin A In Vitro," *Mol. Biol. Cell* 4:79–92 (1993).

Davies, et al., "Human Papillomavirus Type 16 E7 Associates with a Histone H1 Kinase and with p107 through Sequences Necessary for Transformation," *J. Virol.*, 76:2521–8 (1993).

Draetta, et al., "cdc2 Protein Kinase in Complexed with Both Cyclin A and B: Evidence for Proteolytic Inactivation of MPF," *Cell* 56:829–838 (1998).

Dyson, et al., "Homologous Sequences in Adenovirus E1A and Human Papillomavirus E7 Proteins Mediate Interaction with the Same Set of Cellular Proteins," *J. Virol.* 66:6893–6902 (1992).

Dyson, et al., "The Human Papilloma Virus–16 E7 Oncoprotein Is Able to Bind to the Retinoblastoma Gene Product," *Science* 243:934–7 (1989).

Fields, et al., "A novel genetic system to detect protein–protein interactions," *Nature* 340:245–246 (1989).

Fields, "The Two–Hybrid System to Detect Protein–Protein Interactions," *Methods: A Companion to Methods in Enzymology* 5: 116–124 (1993).

Funk, et al., "Inhibiting CDK inhibitors: new lessons from DNA tumor viruses," *Elsevier Science Ltd.* 337–341 (1998).

Funk, et al., "Inhibition of CDK activity and PCNA–dependent DNA replication by p12 is blocked by interaction with the HPV—16 E7 oncoprotein," *Genes & Dev.* 11:2090–100 (1997).

(List continued on next page.)

Primary Examiner—Mary E. Mosher
(74) Attorney, Agent, or Firm—Pharmacia & Upjohn Attorney; James D. Darnley, Jr.

(57) ABSTRACT

The invention provides methods to identify specific inhibitors of HPV E7 binding to CDK2 complex and methods to identify specific inhibitors of E7-induced CDK2 kinase activity. Specific inhibitors identified by the methods, compositions comprising the specific inhibitors, and methods of treatment using the compounds are also provided.

8 Claims, No Drawings

OTHER PUBLICATIONS

Harper, et al., "The p21 Cdk–Interacting Protein Cip1 Is a Potent Inhibitor of G1 Cyclin–Dependent Kinases," *Cell* 75:805–816 (1993).

Houston, et al., "The chemical–biological interface: developments in automated and miniaturised screening technology," *Curr. Opin. Biotechnol.* 8:734–740 (1997).

Jayawickreme, et al., "Gene expression systems in the development of high–throughput screens," *Curr. Opin. Biotechnol.* 8:629–634 (1997).

Jones, et al., "The human papillomavirus E7 oncoprotein can uncouple cellular differentiation and proliferation in human keratinocytes by abrogating $p21^{Cip1-}$mediated inhibition of cdk2,"*Genes & Dev.* 11:2101–11 (1997).

Jones, et al., "Interactions of the human papillomavirus E7 protein with cell cycle regulators," *Cancer Biology* 7:327–337 (1996).

Koonin, "A common set of conserved motifs in a vast variety of putative nucleic acid–dependent ATPhase including MCM proteins involved in the initiation of eukaryotic DNA replication," *Nucl. Acids Res.* 21:2541–7 (1993).

Ma, et al., "Interaction between cyclin–dependent kinases and human papillomavirus replication–initiation protein E1 is required for efficient viral replication," *Proc. Natl. Acad. Sci.* (USA) 96:382–7 (1999).

Massimi, et al., "HPV—16 E7 and adenovirus E1a complex formation with TATA boxing binding protein is enhanced by casein kinase II phosphorylation," *Oncogene* 12:2325–30 (1996).

McIntyre, et al., "Human Papillomavirus E7 Oncoproteins Bind a Single Form of Cyclin E in a Complex with cdk2 and p107," *Virology* 215:73–82 (1996).

Morgan, "Cyclin–Dependent Kinases: Engines, Clocks, and Microprocessors," *Ann. Rev. Cell Dev. Biol.* 13:261–291 (1997).

Mulligan, et al., "The retinoblastoma gene family: cousins with overlapping interests," *Trends Genet* 14:223–9 (1988).

Myers, "Will combinatorial chemistry deliver real medicines?" *Curr. Opin. Biotechnol.* 8:701–707 (1997).

Pei, et al., "HIP—16 E7 protein bypasses keratinocyte growth inhibition by serum and calcium," *Carcinogenesis* 19:1481–6 (1998).

Phelps, et al., "Structure–Function Analysis of the Human Papillomavirus Type 16 E7 Oncoprotein," *J. of Virol.* 66:2418–2427 (1992).

Pietenpol et al., "TGF–β1 Inhibition of c–myc Transcription and Growth in Keratinocytes Is Abrogated by Viral Transforming Proteins with pRB Binding Domains," *Cell* 61:777–85 (1990).

Pines, et al., "Human cyclin A is adenovirus E1A–associated protein p60 and behaves differently from cyclin B," *Nature* 346:760–763 (1990).

Polyak et al., "Cloning of $p27^{Kip1}$, a Cyclin–Dependent Kinase Inhibitor and a Potential Mediator of Extracellular Antimitogenic Signals," *Cell* 78:59–66 (1994).

Ruesch et al., "Human Papillomavirus Oncorproteins Alter Differentiation–Dependent Cell Cycle Exit on suspension in Semisolid Medium," *Virol.* 250:19–29 (1998).

Scheffner, et al., "The E6 Oncoprotein Encoded by Human Papillomavirus Types 16 and 18 Promotes the Degradation of p53," *Cell* 63:1129–36 (1990).

Seedorf, et al., "Human Papillomavirus Type 16 DNA Sequences," *Virol.* 145:181–185 (1985).

Sverdrup, et al., "Replication of Human Papillomavirus (HPV) DNAs Supported by the HPV Type 18E1 and E2 Proteins," *J. Virol.* 68:505–509 (1994).

Tommasino, et al., "HPV16 E7 protein associated with protein kinase $p33^{CDK2}$ and cyclin A," *Oncogene* 8:195–202 (1993).

Toyoshima, et al., "p27, a Novel Inhibitor of G1 Cyclin–Cdk Protein Kinase Activity, Is Related to p21," *Cell* 78:67–74 (1994).

Wu, et al., "The Human Papillomavirus E7 Oncoprotein and the Cellular Transcription Factor E2F Bind to Separate Sites on the Retinoblastoma Tumor Suppressor Protein," *J. Virol.* 67:2402–7 (1993).

Zerfass, et al., "Inactivation of the cdk inhibitor $p27^{KIP1}$ by the human papillomavirus type 16 E7 oncoprotein," *Oncogene* 13:2323–30 (1996).

zur Hausen, "Papillomavirus infections—a major cause of human cancers," *Biochim. Biophys. Acta* 1288:F55–78 (1996).

Desai, et al., "Activation of Human Cyclin–Dependent Kinases In Vitro," *Mol. Biol. Cell.* 3:571–582 (1992).

Roberts, "Evolving Ideas about Cyclins," *Cell* 98:129–132 (1999).

* cited by examiner

METHODS OF IDENTIFYING ANTI-VIRAL AGENTS

This is a Divisional of U.S. application Ser. No. 09/648,215, filed Aug. 25, 2000, now abandoned, which is a continuation-in-part of U.S. patent application Ser. No. 09/382,616 filed Aug. 25, 1999, now U.S. Pat. No. 6,200,746.

FIELD OF THE INVENTION

The invention provides methods to identify anti-viral agents, and more specifically, inhibitors of human papillomavirus E7 protein-induced increase in CDK2 kinase activity.

BACKGROUND

The human papillomaviruses (HPVs) are a family of more than 80 small (approximately 8 kb) DNA viruses that infect stratified squamous epithelia causing warts. Certain high-risk HPV strains, including HPV16, HPV18, and HPV31, have been implicated as the most important etiological agents in cervical cancer [zur Hausen, Biochim. Biophys. Acta 1288:F55–78 (1996)], which is consistent with the observation that E6 and E7 genes from the high risk HPVs are potent oncogenes. Oncogenic potential of E6 and E7 may arise from binding properties to host cell proteins. For example, E6 binds to the tumor-suppressor protein p53 leading to ubiquitin-dependent degradation of the protein [Scheffner, et al., Cell 63:1129–36 (1990)], and E7 binds and promotes degradation of the tumor-suppressor retinoblastoma protein (pRb) [Dyson, et al., Science 243:934–7 (1989); Jones, et al., Genes & Dev 11:2101–11 (1997)]. While E6 and E7 have other activities, their roles in the viral life cycle are not fully elucidated.

The HPV life cycle is regulated in a differentiation-dependent manner within stratified-squamous epithelia [Jones, et al., Genes & Dev 11:2101–11 (1997)]. The virus is maintained as an episome in the basal cell layer, which is the replicating cell population in stratified epithelia. With differentiation of the host cells into keratinocytes, the virus undergoes a burst of DNA replication. Following differentiation, keratinocytes exit the cell cycle and die during the normal course of epithelial stratification. These events are normally irreversible, but HPV E7 activity is sufficient to promote an unscheduled round of DNA synthesis in differentiated keratinocytes [Cheng, et al., Genes & Dev. 9:2335–49 (1995)] The newly synthesized viral DNA is packaged in the upper viable layers of the epithelia, and sloughed into the environment in the dead, differentiated cells. The unscheduled DNA synthesis in differentiated cells is central to the HPV viral life cycle, and the E7 gene product has been implicated as a key viral protein in this event. Consistent with these observations, recent genetic analysis has shown that E7 is required for vegetative replication (amplification) in HPV infected keratinocytes. The E7 gene product is a 98 amino acid protein that binds a number of regulatory proteins, including pRb and proteins in the cyclin-dependent kinase inhibitory protein (KIP) family, the function of which is critical for entry into S-phase entry of the cell cycle [Morgan, Ann. Rev. Cell Dev. Biol. 13:261–291 (1997)].

How E7 promotes progression into S phase has been the subject of intense research because of the importance of this event to the viral life cycle and HPV-related cancer. E7 can overcome negative cellular growth signals including, for example, those mediated by TGF-β [Pietenpol, et al., Cell 61:777–85 (1990)], loss of substrate adherence [Ruesch, et al., Virol. 250:19–29 (1998)], and serum deprivation [Pei, et al., Carcinogenesis 19:1481–6 (1998)]. This activity correlates, in part, with the ability of E7 to transform cells and bind pRb family members [Galloway, et al., Semin. Cancer Biol. 7:309–15 (1996)]. E7 binds other proteins, including, for example transcription factors such as TATA-binding proteins [Massimi, et al., Oncogene 12:2325–30 (1996)], and c-jun and c-fos family members [Antinore, et al., EMBO. J., 15:1950–60 (1996)].

Despite these binding activities, it is unclear which known function(s) of E7, if any, are key for the viral life cycle. Most notably, E7 binds pRb family members [Dyson, et al., Science 243:934–7 (1989); Ciccolini, et al., Oncogene 9:2633–8 (1994); Wu, et al., J. Virol. 67:2402–7 (1993)], p21 [Funk, et al., Genes & Dev 11:2090–100 (1997); Jones, et al., Genes & Dev 11:2101–11 (1997)], and p27 [Zerfass, et al., Oncogene 13:2323–30 (1996)], proteins that participate in the cyclin-dependent kinase phosphorylation pathway regulating cell cycle progression. The cyclin-dependent kinases regulate cell cycle progression by a variety of means [Morgan, Ann. Rev. Cell Dev. Biol. 13:261–291 (1997)], including inhibiting the ability of pRb to sequester E2F [Mulligan, et al., Trends Genet 14:223–9 (1998)], a protein that upregulates a variety of genes required for entry into S phase. E7 binding to p21 and p27, both of which inhibit CDK phosphorylation, results in a net increase in CDK2 activity. These inhibitor proteins have been implicated as key regulators of cell cycle progression that act, at least in part, via a common cyclin-dependent kinase inhibitory domain found in the amino terminus of these proteins [Polyak, et al., Cell 78:59–66 (1994); Chen, et al., Mol. Cell. Biol. 16:4673–82 (1996)]. E7 from viruses with low oncogenic potential lacks these binding activities, suggesting that interaction with one or more cellular proteins is important for neoplastic progression. Whether any of these properties are essential in the viral life cycle is unclear [Davies, et al., J. Virol., 67:2521–8 (1993); Funk, et al., Genes & Dev 11:2090–100 (1997)].

Thus there exists a need in the art to more fully determine mechanisms by which E7 is able promote viral replication and to develop methods to identify inhibitors of E7 specific activity. Inhibition of E7 can result in potent anti-viral activity and therefore, methods to identify inhibitors of E7-dependent activity are desirable.

SUMMARY OF THE INVENTION

The present invention provides methods for identifying anti-viral agents. In a preferred embodiment, methods of the invention identify agents that reduce or inhibit proliferation of human papillomaviruses.

The invention provides methods for identifying an inhibitor of E7-induced CDK2 kinase activity comprising the steps of: a) measuring CDK2 kinase activity on a CDK2 substrate in the presence of human papillomavirus (HPV) E7, or a fragment thereof, and in the presence and absence of a test compound, and b) identifying the test compound as an inhibitor of E7-induced CDK2 kinase activity when decreased phosphorylation of the CDK2 substrate is detected in the presence of the test compound compared to phosphorylation of the CDK2 substrate detected in the absence of the test compound. The CDK2 kinase activity of the invention is that which is detected from a CDK2/cyclin complex as described and exemplified herein. In one aspect, the methods of the invention include use of an E7 fragment that activates CDK2, wherein the E7 fragment consists of a continuous amino terminal fragment of E7 beginning at amino acid residue 1 and terminating at a carboxy terminal residue selected from the group consisting of amino acid residues 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, and 97 as set out in SEQ ID NO. 1. In a preferred embodiment, methods of the invention comprising use of an E7 fragment selected from the group consisting of amino acid residues 1 to 27, amino acid residues 1 to 38, amino acid residues 1 to 48, amino acid residues 1 to 69, amino acid residues 1 to 87 as set out in SEQ ID NO: 1. Methods of the invention preferably include a CDK2 substrate selected from the group consisting of histone H1, HPV protein E1, and HPV protein E2. Methods of the invention include those in which E7 binding to a CDK2 kinase complex is effected through the cyclin component of the CDK2 complex.

The invention also provide methods for identifying an inhibitor of E7-induced CDK2 kinase activity comprising the steps of: a) measuring CDK2 kinase phosphorylation of a substrate; b) measuring increased CDK2 kinase phosphorylation of a substrate in the presence of human papillomavirus (HPV) E7, or a fragment thereof, to determine E7-induced CDK2 kinase activity; c) measuring CDK2 kinase phosphorylation of a substrate in the presence of HPV E7, or a fragment thereof, and in the presence of a test inhibitor compound; and d) identifying the test compound as an inhibitor of E7-induced CDK2 kinase activity when the increased phosphorylation measured in step (b) is reduced in step (c) the presence of the test compound. In one aspect, the methods of the invention include use of an E7 fragment that activates CDK2 wherein the E7 fragment consists of a continuous amino terminal fragment of E7 beginning at amino acid residue 1 and terminating at a carboxy terminal residue selected from the group consisting of amino acid residues 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78 79 80, 81, 82, 83, 84, 85, 86, 87, 88, 89, 90, 91, 92, 93, 94, 95, 96, and 97 as set out in SEQ ID NO. 1. In a preferred embodiment, methods of the invention comprise use of an E7 fragment selected from the group consisting of amino acid residues 1 to 27, amino acid residues 1 to 38, amino residues 1 to 48, amino acid residues 1 to 69, and amino acid residues 1 to 87 as set out in SEQ ID NO: 1. Methods of the invention preferably include a CDK2 substrate selected from the group consisting of histone H1, HPV protein E1, and HPV protein E2.

The invention also provides methods for identifying an anti-viral agent comprising the steps of: a) identifying an inhibitor of E7-induced increase in CDK2 kinase activity; b) measuring viral proliferation in the presence and absence of the inhibitor identified in (a); and c) identifying the inhibitor as an antiviral agent when decreased viral proliferation is detected in the presence of the inhibitor compared to viral proliferation in the absence of the inhibitor.

The invention further provides methods for reducing human papillomavirus (HPV) E7-induced CDK2 kinase activity comprising the step of contacting an HPV infected cell with an inhibitor of E7-induced CDK2 phosphorylation. In another embodiment, the invention provides methods for reducing human papillomavirus (HPV) E7-induced CDK2 kinase activity comprising the step of contacting an HPV infected cell with an inhibitor of E7 binding to CDK2 kinase complex.

The invention also provides methods for ameliorating human papillomavirus (HPV) proliferation comprising the step of administering to an individual in need thereof an effective amount of an inhibitor of HPV E7-induced CDK2 kinase activity. In another aspect, the invention provide methods for ameliorating human papillomavirus (HPV) proliferation comprising the step of administering to an individual in need thereof an effective amount of an inhibitor of HPV E7 binding to CDK2 kinase complex.

DETAILED DESCRIPTION OF THE INVENTION

Methods of the invention include use of viral proteins that induce CDK2 kinase activity. Preferably, the viral proteins used in methods of the invention are HPV E7 (as exemplified herein) or other viral proteins which are at least 35%, at least 40%, at least 45%, at least 50%, at least 55%, at least 60%, at least 65%, at least 70%, at least 75%, at least 80%, at least 85%, at least 90%, at least 95%, or at least 99% homologous to E7 Cr1 and/or CR2 regions. Homology can be determined, for example, using basic BLAST search analysis with default parameters. Exemplary viral proteins with homology to the CR1 and/or CR2 regions of E7 include adenovirus E1A and SV-40 T antigen.

The invention provides methods for identifying an inhibitor of E7-induced CDK2 kinase activity comprising the steps of: a) measuring CDK2 kinase activity on a CDK2 substrate in the presence of human papillomavirus (HPV) E7, or an E7 fragment thereof, and in the presence and absence of a test compound, and b) identifying the test compound as an inhibitor of E7-induced CDK2 kinase activity when decreased phosphorylation of the CDK2 substrate is detected in the presence of the test compound compared to phosphorylation of the CDK2 substrate detected in the absence of the test compound. E7-induced CDK2 kinase activity is the increased phosphorylation of a CDK2 substrate observed when the CDK2 complex is contacted with E7 in the absence of a CDK2 kinase inhibitor (e.g., p21 and/or p27), compared to CDK2 substrate phosphorylation observed in the absence of E7 and a CDK2 kinase inhibitor. Thus, optionally CDK2 kinase activity in the absence of E7 may be determined as a control. In one aspect, the methods of the invention include use of an E7 (including other viral E7 homologs or orthologs that induce CDK2 activity) fragment or variant thereof that activates the CDK2 complex. Exemplary E7 fragment consists of a continuous amino terminal fragment of E7 beginning at amino acid residue 1 and terminating at a carboxy terminal residue selected from the group consisting of amino acid residues 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, and 97 as set out in SEQ ID NO. 1. In a preferred embodiment, methods of the invention comprise use of an E7 fragment selected from the group consisting of amino acid residues 1 to 27, amino acid residues 1 to 38, amino acid residues 1 to 48, amino acid residues 1 to 69, and amino acid residues 1 to 87 as set out in SEQ ID NO: 1. E7 variants as used herein include E7 proteins comprising additions, deletions, substitutions and other covalent modifications that result in a E7 polypeptide distinct from naturally occurring E7 but retaining the ability to induce CDK2 kinase activity. Methods of the invention preferably include a CDK2 substrate selected from the group consisting of histone H1, HPV protein E1 and HPV protein E2, however methods of the invention also include use of any physiological, non-physiological, or synthetic substrate of CDK2. Synthetic substrates encompass non-naturally occurring fragments, analogs and variants of naturally occurring CDK2 substrates. In preferred embodiments, methods of the invention are performed in the absence of CDK2 inhibitor proteins such as p21 and p27, thereby providing for E7-induced kinase activity, rather than E7-induced reduction in CDK2 inhibition.

The invention also provide methods for identifying an inhibitor of E7-induced CDK2 kinase activity comprising the steps of: a) measuring CDK2 kinase phosphorylation of a substrate; b) measuring increased CDK2 kinase phosphorylation of a substrate in the presence of human papillomavirus (HPV) E7, or a fragment thereof, to determine E7-induced CDK2 kinase activity; c) measuring CDK2 kinase phosphorylation of a substrate in the presence of HPV E7, or a fragment thereof, and in the presence of a test inhibitor compound; and d) identifying the test compound as an inhibitor of E7-induced CDK2 kinase activity when the increased phosphorylation measured in step (b) is reduced in step (c) in the presence of the test compound. In one aspect, the methods of the invention include use of an E7 fragment that activates CDK2 kinase activity wherein the E7 fragment consists of a continuous amino terminal fragment of E7 beginning at amino acid residue 1 and terminating at a carboxy terminal residue selected from the group consisting of amino acid residues 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 ,80, 81, 82, 83, 84, 85, 86, 87, 88, 89, 90, 91, 92, 93, 94, 95, 96, and 97 as set out in SEQ ID NO. 1. In a preferred embodiment, methods of the invention comprising use of an E7 fragment include an E7 fragment selected from the group consisting of amino acid residues 1 to 27, amino acid residues 1 to 38, amino acid residues 1 to 48, amino acid residues 1 to 69, and amino acid residues 1 to 87 as set out in SEQ ID NO: 1. Methods of the invention preferably include a CDK2 substrate selected from the group consisting of histone H1, HPV protein E1 and HPV protein E2. Components of the CDK2 complex which produces the CDK2 kinase activity may include cyclins, e.g., members of the A family including for example, A1 and A2, members of the B family including, for example B1 and B2, cyclin C, members of the D family including for example, D1, D2, and D3, members of the E family including for example, E1, E2 and Es, cyclin F, members of the G family including for example, G1 and G2, cyclin H, cyclin I, cyclin L, and members of the T family including for example T1, T2a, and T2b to the extent that the cyclin binds CDK2 and participates in effecting CDK2 kinase activity.

Methods of the invention comprehend use of CDK2 complex proteins, E7 and/or CDK2 substrate compounds from naturally occurring sources as well as from recombinant sources transformed or transfected with one or more polynucleotides encoding the desired recombinant product (s). Fragments of E7 that induce CDK2 kinase activity are also embraced. Preferably the CDK2 complex, E7 (or fragment thereof) and/or CDK2 substrate compounds are recombinant products. The compounds can also be produced by methods that facilitate purification, i.e., as fusion proteins comprising labels or tags thereby permitting production of significantly pure compounds. Preferred labels or tags include glutathione-S-transferase sequences (which permit purification using glutathione agarose) or poly-histidine regions (permitting purification using nickel affinity chromatography). Other labels and tags well known and routinely used in the art are also contemplated. The invention also embraces, however, methods employing crude preparations of E7, CDK2 complex, and CDK2 substrate, but essentially free of other human proteins.

Numerous embodiments of the methods of the invention are carried out in order to detect a decrease in E7-induced CDK2 kinase activity in the presence of a test compound that prevents, reverses, or destabilizes binding between E7 (or a fragment thereof) and the CDK2 complex. Preferred methods of this type are performed in solution assays, and changes in kinase activity are measured in the presence and absence of a test compound. Solution kinase assays of this type, e.g., histone kinase assays, are well known and routinely practiced in the art.

Methods of the invention include those wherein either E7 (or a fragment, variant, or analog thereof that retains the ability to induce CDK2 kinase activity) or bind the CDK2 complex is immobilized on a solid support and E7 (or a fragment, analog, or variant thereof) or the CDK2 complex, whichever is not immobilized, is detectably labeled. Binding between the two compounds is examined in the presence and absence of a test compound and a change in the amount of bound detectable label is measured. In assays wherein a lower amount of bound label is detected in the presence of the test compound, the test compound is identified as an inhibitor of E7 binding to the CDK2 complex. Subsequent kinase assays can be employed to determine the effect of the test compound on kinase activity.

The invention also comprehends cell-based assays wherein inhibitors of E7 and CDK2 complex binding can be identified, as well as inhibitors of E7-enhanced phosphorylation. In one aspect, the invention provides split hybrid assays as generally described in WO 98/13502, published Apr. 2, 1998, incorporated by reference herein, wherein, for example, (i) components of the CDK2 complex are expressed as a fusion protein with amino acid sequences comprising either a transcription factor DNA binding domain or a transcription factor transactivating domain, and (ii) E7 (or a fragment thereof) is also expressed as a fusion protein with whichever transcription factor domain is not fused to the CDK2 complex protein. Binding between the CDK2 complex and E7 fusion proteins brings into proximity the two components of the transcription factor to produce a biologically active transcription factor. A plasmid encoding a repressor gene is also introduced into the same cell type and expression of the repressor is driven by a transcription element recognized by the biologically active transcription factor comprising the two fusion proteins. The expressed repressor then acts to prevent transcription of a reporter gene. In the presence of a compound that inhibits binding between the E7 and CDK2 complex fusion proteins, the biologically active transcription factor is not formed, the repressor protein is not expressed, and transcription of the reporter gene is permitted. In assays of this type, inhibition of a specific binding interaction is detected by a positive signal, i.e., expression of a detectable reporter gene. The invention also embraces numerous variations on this method as described in WO 95/20652, published Aug. 3, 1995, incorporated by reference herein. In addition, the invention embraces di-hybrid, or two-hybrid assays as previously described [Fields and Song, *Nature* 340:245–246 (1989); Fields, *Methods: A Companion to Methods in Enzymology* 5:116–124 (1993); U.S. Pat. No. 5,283,173 issued Feb. 1, 1994 to Fields, et al.], wherein inhibition of a specific binding interaction is detected by a negative signal, i.e., loss or expression of a reporter gene. Modifications and variations on the di-hybrid assay (also referred to in the art as "two-hybrid" assays) have previously been described [Colas and Brent, *TIBTECH* 16:355–363 (1998)] and are embraced by the invention. In a cell-based assay, however, detection of inhibition of binding with a positive signal is preferable.

In another aspect, cell based assays are provided wherein E7 and components of the CDK2 kinase complex are expressed (or overexpressed) in a cell and inhibitors identified which decrease E7-enhanced phosphorylation. Optionally, detection of E7-enhanced phosphorylation can be accomplished using a control cell line which expresses CDK2 kinase complex components in the absence of E7. Kinase activity in this control cell would identify the basal level of kinase complex activity. Cell lines for assays of this type may be produced through introduction of exogenous DNA encoding E7 and/or components of the CDK2 complex or introducing exogenous DNA which increases expression of one or more of these assay component which are encoded in the endogenous cellular genome.

Assays of the invention are particularly amenable to high throughput screening (HTS) assays. HTS permit screening of large numbers (i.e., tens to thousands or more) of compounds in an efficient manner. Cell-based HTS systems are also embraced, including melanophore assays, yeast-based assay systems, and mammalian cell expression systems [Jayawickreme and Kost, *Curr. Opin. Biotechnol.* 8:629–634 (1997)]. Automated and miniaturized HTS assays are particularly preferred [Houston and Banks, *Curr. Opin. Biotechnol.* 8:734–740 (1997)]. HTS assays are designed to identify "hits" or "lead compounds" having the desired inhibitory property, from which modifications can be designed to improve the desired property. Chemical modification of the "hit" or "lead compound" is often based on an identifiable structure/activity relationship between the "hit" and one or more of the binding partner polypeptides.

There are a number of different libraries used for the identification of specific small molecule inhibitors, including, (1) chemical libraries, (2) natural product libraries, and (3) combinatorial libraries comprised of random peptides, oligonucleotides or organic molecules.

Chemical libraries consist of structural analogs of known compounds or compounds that are identified as "hits" or "leads" via natural product screening. Natural product libraries are derived from collections of microorganisms, animals, plants, or marine organisms which are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof. For a review, see *Science* 282:63–68 (1998), incorporated by reference herein. Combinatorial libraries are composed of large numbers of peptides, oligonucleotides or organic compounds as a mixture. They are relatively easy to prepare by traditional automated synthesis methods, PCR, cloning or proprietary synthetic methods. Of particular interest are peptide and oligonucleotide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, *Curr. Opin. Biotechnol.* 8:701–707 (1997), incorporated by reference herein.

The invention further provides specific inhibitors identified by the methods of the invention. Specific inhibitors are defined as those that act to preclude, reverse or disrupt E7 binding to CDK2 complex (or CDK2 kinase activity), and/or prevent, reverse or disrupt E7-induced increase in CDK2 kinase activity. Compositions comprising a specific inhibitor of E7-induced CDK2 kinase activity and a pharmaceutically acceptable carrier are also provided. Preferably, compositions of the invention are pharmaceutical compositions. The invention also provides use of an inhibitor of E7 binding to the CDK2 complex in the production of a medicament for ameliorating viral infection, e.g., HPV infection, adenoviral infection, or SV40 infection.

The pharmaceutical compositions of the invention optionally may include pharmaceutically acceptable (i.e., sterile and non-toxic) liquid, semisolid, or solid diluents that serve as pharmaceutical vehicles, excipients, or media. Any diluent known in the art may be used. Exemplary diluents include, but are not limited to, polyoxyethylene sorbitan monolaurate, magnesium stearate, methyl- and propylhydroxybenzoate, talc, alginates, starches, lactose, sucrose, dextrose, sorbitol, mannitol, gum acacia, calcium phosphate, mineral oil, cocoa butter, and oil of theobroma.

The pharmaceutical compositions can be packaged in forms convenient for delivery. The compositions can be enclosed within a capsule, sachet, cachet, gelatin, paper, or other container. These delivery forms are preferred when compatible with entry of the composition into the recipient organism and, particularly, when the composition is being delivered in unit dose form. The dosage units can be packaged, e.g., in tablets, capsules, suppositories or cachets.

The invention also provides methods for identifying an anti-viral agent comprising the steps of: a) identifying an inhibitor of E7-induced increase in CDK2 kinase activity; b) measuring viral proliferation in the presence and absence of the inhibitor identified in (a); and c) identifying the inhibitor as an antiviral agent when decreased viral proliferation is detected in the presence of the inhibitor compared to viral proliferation in the absence of the inhibitor. In one aspect, methods to identify an inhibitor of E7-induced CDK2 kinase activity are utilized to screen test compounds for use as antiviral agents. The inhibitors identified are utilized in assays that permit determination of the inhibitor's ability to act as an anti-viral agent in, for example, cell-based assays (i.e., cell culture systems) and/or animal models of HPV viral infection.

Another aspect of the invention provides methods for inhibiting E7-induced CDK2 kinase activity comprising the steps of administering to an individual in need thereof an effective amount of an inhibitor of E7-induced CKD2 kinase activity or an inhibitor of E7 binding to the CDK2 complex. Also provided are methods for ameliorating (inhibiting) viral proliferation comprising the steps of administering to an individual in need thereof an effective amount of an inhibitor of E7-induced CKD2 kinase activity or an inhibitor or E7 binding to the CDK2 complex. The invention further provides methods for preventing or treating viral infection comprising the steps of administering to an individual in need thereof an effective amount of an inhibitor of E7-induced CKD2 kinase activity or an inhibitor of E7 binding to the CDK2 complex. Preferably, the individual in need thereof is administered a pharmaceutical composition of the invention. The pharmaceutical compositions may be introduced into the subject to be treated by any conventional method including, e.g., by intravenous, intradermal, intramuscular, intramammary, intraperitoneal, intrathecal, intraocular, retrobulbar, intrapulmonary (e.g., aerosolized drug solutions) or subcutaneous injection (including depot administration for long term release); by oral, sublingual, nasal, anal, vaginal, or transdermal delivery; or by surgical implantation, e.g., embedded under the splenic capsule, brain, or in the cornea. The treatment may consist of a single dose or a plurality of doses over a period of time. Co-administration of other anti-viral agents including, e.g., acyclovir, gancyclovir, vidarabidine, foscarnet, cidofovir, amantidine, ribavirin, trifluorothymidine, interferon-α, zidovudine, didanosine or zalcitabine, is also contemplated.

When given parenterally, specific binding inhibitor compositions are generally injected in doses ranging from 1 μg/kg to 100 mg/kg per day, preferably at doses ranging from 0.1 mg/kg to 50 mg/kg per day, and more preferably at doses ranging from 1 to 20 mg/kg/day. The inhibitor composition may be administered by an initial bolus followed by a continuous infusion to maintain therapeutic circulating levels of a drug product. Those of ordinary skill in the art will readily optimize effective dosages and administration regimens as determined by good medical practice and the clinical condition of the individual patient. The frequency of dosing will depend on the pharmacokinetic parameters of the agents and the route of administration. The optimal pharmaceutical formulation will be determined by one skilled in the art depending upon the route of administration and desired dosage. See for example, Remington's Pharmaceutical Sciences, 18th Ed. (1990, Mack Publishing Co., Easton, Pa. 18042) pages 1435–1712, the disclosure of which is hereby incorporated by reference. Such formulations may influence the physical state, stability, rate of in vivo release, and rate of in vivo clearance of the administered agents. Depending on the route of administration, a suitable dose may be calculated according to body weight, body surface area, or organ size. Further refinement of the calculations necessary to determine the appropriate dosage for treatment involving each of the above-mentioned formulations is routinely made by those of ordinary skill in the art without undue experimentation, especially in light of the dosage information and assays disclosed herein, as well as the pharmacokinetic data observed in human clinical trials. Appropriate dosages may be ascertained through use of established assays for determining blood levels dosages in conjunction with appropriate dose-response data. The final dosage regimen will be determined by the attending physician, considering various factors which modify the action of drugs, e.g., the drug's specific activity, the severity of the damage and the responsiveness of the patient, the age, condition, body weight, sex and diet of the patient, the severity of any infection, time of administration and other clinical factors. As studies are conducted, further information will emerge regarding the appropriate dosage levels and duration of treatment for various diseases and conditions.

It will be appreciated that the pharmaceutical compositions and treatment methods of the invention may be useful in the fields of human medicine and veterinary medicine. Thus, the subject to be treated may be a mammal, preferably human, or other animals. For veterinary purposes, subjects include, for example, farm animals including cows, sheep, pigs, horses, and goats, companion animals such as dogs and cats; exotic and/or zoo animals; laboratory animals including mice, rats, rabbits, guinea pigs, and hamsters; and poultry such as chickens, turkeys, ducks and geese.

EXAMPLES

The invention is illustrated by the following examples. Example 1 relates binding assays that characterize E7 interactions with various proteins. Example 2 describes kinase assays wherein the effect of E7 on CDK2 activity examined. Example 3 relates to the effects of HPV E7 on various kinases. Example 4 describes kinetics of E7-induced activation of CDK2. Example 5 addresses identification of E7 amino acid residues required for CDK2 activation. Example 6 describes interaction of E7 with cyclinA.

Example 1

E7 Binding Assays

In an attempt to characterize HPV E7 binding interactions, assays were designed using either HPV6b E7, HPV16 E7 or HPV31 E7 and various cellular proteins or fragments thereof. The E7 proteins were expressed as glutathione-S-transferase (GST) fusion proteins in order to facilitate purification and expression constructs were prepared as follows.

E7 Expression Constructs

The E7 gene was amplified by polymerase chain reaction (PCR) from cloned HPV31, HPV16, and HPV6b DNA (American Type Culture Collection [ATCC] for HPV 31 and HPV 6b; Seedoff et al., Virol. 145:181–185 (1985) for HPV 16, also available from the ATCC). PCR primers, as set out below, were designed to engineer BamHI or XhoI sites in the amplification product to facilitate in-frame subcloning into expression vector pGEX-4T-3 (Pharmacia Biotech). The vector was used to express the product of each subcloned sequence as a fusion protein with a glutathione-S-transferase (GST) moiety at the amino-terminus.

HPV31 primers
E7 Sense (with a BamHI site) SEQ ID NO: 2
CGGGATCCATGCGTGGAGAAACACCTAC
E7 Antisense (with a BamHI site) SEQ ID NO: 3
CGGGATCCTTACAGTCTAGTAGAACAG
HPV 6b primers
E7 Sense (with a BamHI site) SEQ ID NO: 4
CGGGATCCATGCATGGAAGACATGTT
E7-Antisense (with an XhoI site) SEQ ID NO: 5
CCGCTCGAGTTAGGTCTTCGGTGCGC
HPV 16 primers
E7 Sense (with a BamHI site) SEQ ID NO: 6
CGGGATCCATGCATGGAGATACACCTAC
E7 Antisense (with an XhoI site) SEQ ID NO: 7
CCGCTCGAGTTATGGTTTCTGAGAACAGATG For HPV31E7, the amplification product was subcloned into pGEX-4T-3 previously digested with BamHI, while HPV6b and HPV16 E7 amplification products were subcloned into pGEX-4T-3 previously digested with BamHI and XhoI. Proper orientation was determined using restriction mapping, sequence analysis was carried out using Perkin-Elmer ABI-Prism® technology, and the expression constructs were individually transfected into a JM 109 strain of E. coli. Bacteria in log-growth phase were harvested by centrifugation after a four hour induction with 0.5 mM IPTG at 30° C. The cell pellet was resuspended in lysis buffer containing 11.3 mM $NaH_2PO_4$, 38.7 mM $Na_2HPO_4$, 0.07% β-mercaptoethanol, 10 mM EDTA, 0.5 mM PMSF, 0.025 IU/ml aprotinin, and 10 nM leupeptin, and protein was purified using glutathione-agarose beads (Sigma) according to manufacturer's suggested protocol. After extensive washing with PBS, the GST-E7-coupled beads were stored at 4° C. until use. Protein levels were measured using a BioRad protein assay kit, and purified protein preparations were examined by SDS-PAGE followed by Coomassie blue staining and Western blotting.

Binding Protein Expression Constructs

Full length E7-binding proteins p21 and p27 were expressed with poly-histidine tags to facilitate purification. Histidine-tagged fragments of p21 and p27 were also expressed comprising amino terminal residues 1–78 of p21 (designated His-p21N), carboxy terminal residues 72–164 of p21 (designated His-p21C), amino terminal residues 1–101 from p27 (designated His-p27N) or carboxy terminal residues 95–198 of p27 (designated His-p27C). Expression constructs encoding the full length proteins or fragment polypeptides were prepared as follows.

The full-length, histidine-labeled p21 protein, designated His-p21, was subcloned as a XhoI/BamHI PCR fragment into pET15b (Novagen) previously digested with the same two enzymes. Template DNA was the cloned p21 coding sequence [Harper et al., Cell 75:805–816 (1993)] and primers included p-21-1' and p21-4' to amplify the full length p21 coding region. The p21 amino and carboxy terminal histidine-tagged fragments were also amplified by PCR to produce XhoI/BamHI fragments using primers p21-1' and p21-2' to amplify sequences encoding residues 1 to 78, and p21-3' and p21-4' to amplify the region encoding residues 72 to 164.

p21-1' GCCTCGAGATGTCAGAACCGGCTGGG-GATG SEQ ID NO: 8 p21-2' GCGGATCCTTAGAAGGTAGAGCT-TGGGCAG SEQ ID NO: 9 p21-3' GCCTCGAGCTGCCCAAGCTCTACCTTC SEQ ID NO: 10 p21-4' GCGGATCCTTAGGGCTTCCTCTTGGAG SEQ ID NO: 12

Amplification reactions were carried out using Ready-to-Go™ PCR Reaction Beads (Amersham-Pharmacia Biotech) according to the manufacturer's suggested protocol Reaction products were digested with BamHI and XhoI, extracted with equal volumes of phenol and chloroform, precipitated with ethanol, and suspended in 20 µl water. Ligation into vector pET15b (Novagen) was carried out overnight at 15° C. in a reaction containing 5 µl PCR amplification product, 2 µl vector DNA (previously digested with BamHI and XhoI, 2 µl 5× ligation buffer (BRL) and 1 µl T4 ligase. Clones having proper orientation were selected and their sequences confirmed by restriction analysis and PCR sequencing using ABI-PRISM®® (PE Applied Biosystems) technology.

Similarly, the histidine labeled, full-length p27 protein, designated His-p27, was subcloned as a XhoI/BamHI PCR fragment into pET15b (Novagen) previously digested with the same two enzymes. DNA encoding human p27 [Toyoshima and Hunter, Cell 78:67–74 (1994)] was used as template in an amplification reaction with primer pairs p27-1 and p27-5 to amplify the full length p27 cDNA. The same template DNA was used to amplify polynucleotides encoding the histidine-labeled amino and carboxy terminal fragments of p27, with primer pair p27-7 and p27-8 used to amplify DNA encoding p27 residues 1 to 101, and primer pair p27-9 and p27-10 used to generate a DNA encoding residues 95 to 198.

p27-1 CGGATCCTATGTCAAACGTGCGAGTG SEQ ID NO: 11 p27-5 AGGATCCTTACGTTTGACGTCTTCTG SEQ ID NO: 13 p27-7' GCCTCGAGATGTCAAACGTGCGAGTGTC SEQ ID NO: 14 p-27-8' GCGGATCCTTACACCTTGCAGGCAC-CTTTG SEQ ID NO: 15 p27-9' GCCTCGAGAAAGGTGCCTGCAAGGTGC SEQ ID NO: 16 p27-10' GCGGATCCTTACGTTTGACGTCTCTG SEQ ID NO: 17

All PCR amplifications were carried out using Ready-to-Go™ PCR Reaction Beads (Amersham-Pharmacia Biotech) according to the manufacturer's suggested protocol.

In producing the full length p27 expression vector, the PCR amplification product was first subcloned into vector pCRII using a TA cloning kit (Invitrogen) according to the manufacturer's suggested protocol. The full length cDNA was removed from the vector with BamHI digestion and the sequence isolated using 1% agarose gel electrophoresis. The full length band was excised from the gel and the fragment purified using a GeneClean® kit (Bio 101) according to the manufacturer's suggested protocol. The isolated fragment was subcloned into vector pTrcHisB (Invitrogen) previously digested with BamHI, and ligation was carried out using 5 µl digested PCR product, 2 µl vector, 2 µl 5× ligation buffer (BRL), and 1 µl T4 ligase (BRL). The ligation reaction was used to transform JM 109 competent cells according to standard transformation protocols.

For cloning p27 DNA fragments encoding residues 1 to 101 and 95 to 198, PCR products were digested with BamHI and XhoI, extracted with equal volumes of phenol and chloroform, precipitated with ethanol, and resuspended in water. Ligation was carried out as described above, and the ligation products were used to transform E. coli strain DH5α. Clones were selected and orientation determined by restriction analysis and PCR sequencing using ABI-PRISM® technology.

Expression constructs encoding the histidine-tagged proteins were transformed into E. coli strain BL21(DE3) using standard techniques and expressed proteins were purified using nickel agarose affinity chromatography under denaturing conditions. Eluted proteins were refolded by extensive, step-wise dialysis using techniques well known in the art.

Preparation of HEK293 Cell Lysate

HEK293 cells were collected by centrifugation, washed twice in phosphate buffered saline, resuspended in three volumes of low salt buffer containing 20 mM HEPES, pH 7.9, 10 mM KCl, 0.1 mM sodium vanadate, 1 mM EDTA, 1 mM EGTA, 0.1% NP-40® and 10% glycerol, and incubated on ice for 10 minutes. Cells were centrifuged at 13,000×g and supernatant containing the cytoplasmic extract was collected. The pellet, containing the nuclei, was washed once in the low salt buffer, and suspended in three volumes of a high salt buffer containing 20 mM HEPES, pH 7.9, 420 mM NaCl, 10 mM KCl, 0.1 mM sodium vanadate, 1 mM EDTA, 1 mM EGTA, 0.1% NP-40® and 10% glycerol. The nuclear suspension was incubated with agitation at 4° C. and centrifuged at 13,000×g, after which the nuclear lysate was collected and stored until use. In precipitation assays (described below), nuclear extract was mixed with cytoplasmic extract at a ratio of 1:2.

Binding Assay Conditions

GST-16E7 or GST-31E7 fusion proteins bound to glutathione-agarose beads were incubated with either purified pRb (QED Bioscience Inc.), His-p21, His-p21N, His-p21C, His-p27, His-p27N, His-p27C, or HEK293 cell lysate at 4° C. for two hours in binding buffer containing 20 mM HEPES, pH 7.4, 10 mM KCl, 1 mM EDTA, 1 mM EGTA, 140 mM NaCl, 13% glycerol, 1 mM DTT, and 1× protease inhibitor tablet (Boehringer Mannheim). After washing five times with binding buffer, the glutathione-agarose beads were resuspended in SDS-sample buffer and heated to 100° C. to elute binding proteins. Eluted proteins were separated using 15% SDS-PAGE and the proteins were analyzed by Coomassie blue staining and Western blotting.

Results indicated that GST-31E7 bound purified pRb as well as pRb in HEK 293 cell lysate. E7 proteins from the HPV strains were found to bind recombinant forms of both p21 and p27, consistent with previous observations [Funk, et al., Genes & Dev 11:2090–100 (1997); Jones, et al., Genes & Dev 11:2101–11 (1997), Zerfass, et al., Oncogene 13:2323–30 (1996)]. However, neither amino- or carboxy-terminal fragments of p21 or p27 were able to significantly bind E7 relative to the full length molecule, suggesting that neither the carboxy- or amino-terminal halves of p21 or p27 are sufficient for E7 binding.

Example 2

Kinase Assays

Kinase assays were performed with CDK2 co-expressed with cyclin E or cyclin A from baculovirus vectors in Sf9 cells as described below.

Baculovirus Vector Construction

Recombinant cyclin E and cyclin A was prepared as follows. DNA encoding cyclin E was cloned from human liver cDNA using primers KW133 and PH 113 designed based on the published sequence.

KW133 GATCAGATCTCATGAAGGAGGACGGCG-GCG SEQ ID NO: 18

RH113 GCAGATCTTCAGTGGTGGTGGTGGTG-GTGG SEQ ID NO: 19

The cyclin E amplification product was modified in the PCR to introduce aberrant nucleotides with the 3' RH113 primer producing a hyperstable form of the protein. The amplification product was inserted into vector pAcGHLT-C (PharMingen) which expresses encoded proteins as a GST fusion.

The cyclin A gene [Pines and Hunter, Nature 346:760–763 (1990)] was amplified by PCR from using primers RH101 and RH103 that introduced NotI restriction sites flanking the fusion gene amplification product.

RH102 GGGCGGCCGCATGTCCCCTATACTAGGT-TAT SEQ ID NO: 20

RH103 GGGCGGCCGCGTCAGTCAGTCACGATG SEQ ID NO: 21

The amplification product was subcloned into baculovirus transfer vector pVL1392 (PharMingen) which expresses encoded proteins as GST fusions. Restriction mapping identified clones with correct insert orientation, and one clone, pVL-GST-cyclin A, was sequenced and verified to be wild-type.

Baculovirus Expression

Recombinant baculoviruses were produced by co-transfection of *Spodoptera frugiperda* cells (Sf9) with cyclin transfer vectors and BaculoGold crippled baculoviral DNA (PharMingen) according to manufacturer's suggested protocol. Resultant viruses were purified through three consecutive plaque purifications. A baculovirus expressing CDK2 with a hemagglutinin tag as previously described (Desai et al., Mol. Biol. Cell 3: 571–582) was used for CDK2 expression.

Purification of Cyclin/CDK2 Complexes

Cyclin E and cyclin A were co-expressed with CDK2 by co-infection of either Sf9 or High Five™ (Invitrogen) cells with the recombinant baculoviruses at a multiplicity of infection (m.o.i.) of 20 for the cyclin-expressing viruses and 10 for the CDK2-expressing virus. Sf9 cells were grown at 28° C. in spinner flasks in Grace's medium (GIBCO/BRL) containing 10% fetal bovine serum (FBS), 100 units/ml penicillin, and 100 μg/ml streptomycin. High Five cells were grown at 28° C. in shaker flasks at 150 r.p.m. in InsectEX-PRESS™ medium (Bio Whittaker).

Cells were collected by centrifugation, cell pellets were washed with phosphate buffered saline (PBS), and the cells were resuspended in hypotonic lysis buffer containing 10 mM HEPES, pH 7.4, 10 mM NaCl, 1 mM EDTA, 0.2 μg/ml leupeptin, 0.2 μg/ml pepstatin, 0.2 μg/ml aprotinin, and 0.2 mM AEBSF at a density of 1 ml for each $10^7$ cells initially infected. After an hour, NaCl was added to a final concentration of 150 mM. Cells were sonicated on ice for two minutes (100% duty cycle with an output of 4) and the lysate was clarified by centrifugation. The GST-cyclin/CDK2 complexes were isolated by affinity chromatography using glutathione-Sepharose® beads (Pharmacia Biotech). The beads were washed extensively with PBS and the complexes eluted with 15 mM reduced glutathione in 50 mM Tris-HCl, pH 8.0. Eluted protein was analyzed by SDS-PAGE and Western blotting to confirm purity of the cyclin A- and cyclin E-CDK2 complexes.

MBP-E1 and MBP-E2 Expression and Purification

A maltose-binding protein (MBP)-E1 fusion protein expression vector was constructed as follows. Briefly, the vector was constructed by amplifying the HPV18 E1 gene from pSGE1-18 [Sverdrup and Khan, *J. Virol.* 68:505–509 (1994)] and cloning the resulting amplification product into pMAL-CR1 (New England Biolabs, Inc.) previously digested with BamHI. Primers to the 5' and 3' ends of the E1 gene incorporated BamHI or BglII sites into the amplification product. The resulting vector encoded an inducible MBP-E1 fusion protein.

The MBP-E1 fusion protein was purified according to the manufacturer's suggested protocol. Briefly, *E. coli* strain DH5 expressing recombinant MBP-E1 fusion protein was fermented at the four liter scale. Cells were collected by centrifugation, the cell pellet was resuspended in column buffer containing 20 mM HEPES, pH 7.4, 200 mM NaCl, 1 mM EDTA, 10% glycerol, and 5 mM β-mercaptoethanol, and the cells were lysed using an Avestin Emulsiflex™ dynamic homogenizer at 15,000 to 20,000 psi. The lysate was centrifuged at 25,000×g for 60 minutes at 5 to 8° C., and the supernatant was filtered through a 0.45 μm filter. The filtered supernatant was loaded onto a 2.6 cm amylose-affinity column containing 50 ml amylose resin (New England BioLabs). The column was washed with 12 bed volumes of column buffer and eluted using 10 mM maltose in column buffer. Eluate fractions were analyzed for purity using SDS-PAGE.

A construct encoding an E2 maltose-binding fusion protein was prepared in a similar manner.

Kinase Assay

Histone H1 was chosen as the substrate in the kinase assays since pRb, a physiological CDK2 substrate, is known to bind E7 and could interfere with the assay. When indicated, His-p27 was added at a concentration previously demonstrated to inhibit 50% of the CDK2 kinase activity.

GST-E7 fusion proteins were prepared as described above and eluted from the glutathione-agarose beads using buffer containing 50 mM Tris-HCl (pH 8.0), 5 mM reduced glutathione, 0.1% Triton® X-100, 1 mM DTT, and 1× protease inhibitor tablet (Boehringer Mannheim).

For some assays, HEK293 cell lysate (100 μg total protein, prepared as described above) was preincubated with purified GST-31E7 protein in PBS in the presence of p13 agarose beads (Calbiochem) at 4° C. for one hour, and subsequently incubated with purified His-p27 for 30 min at 4° C. Preincubation was carried out to permit protein complex formation, while p13 agarose beads bind cyclin-dependent kinase complexes to facilitate purification [Dreatta, et al., *Cell* 56:829–838 (1989)]. After collection and washing four times with PBS, the beads were washed two additional times with KIP buffer containing 50 mM Tris-Cl, pH 7.5, 10 mM $MgCl_2$, 5 mM EGTA, 2 mM DTT, and 10 μM ATP. The beads were resuspended in 35 μl KIP buffer, mixed with 35 μl histone kinase buffer containing 0.6 mg/ml histone H1, 0.2 mM ATP, 5 μCi [γ-$^{32}$P]-ATP/assay, 40 mM HEPES, pH 7.3, 10 mM EGTA, and 20 MM $MgCl_2$, and incubated at room temperature for 20 minute. The reaction was stopped by adding 70 μl of 2× SDS-sample buffer. Phosphorylated proteins were analyzed by SDS-PAGE followed by autoradiography and PhosphorImager® analysis.

In other assays, purified cyclin A- or cyclin E-complexed CDK2 was included. GST-E7 was added directly to purified recombinant cyclin/CDK2 complex in kinase buffer (20 mM MgCl, 10 mM EGTA, and 40 mM HEPES, pH 7.0) and incubated on ice for 20 min prior to beginning the kinase assay. In some assays, GST-E7 was preincubated with p21 or p27. Kinase activity was measured following addition of 1 μl of 2 mCi/ml [γ-$^{32}$P] ATP and 3.75 μg histone H1 per 30 μl assay and incubation at 30° C. for 20 min. The reaction was stopped by adding SDS sample buffer, and phosphorylated proteins were analyzed by SDS-PAGE followed by autoradiography and PhosphorImager® analysis.

Results indicated that E7 had little or no effect on p21- and p27-dependent inhibition of cyclin E/CDK2 activity, and these observations were inconsistent with previous reports that E7 significantly blocks p21 [Funk, et al., Genes & Dev 11:2090–100 (1997); Jones, et al., Genes & Dev 11:2101–11 (1997)], and/or p27 [Zerfass, et al., Oncogene 13:2323–30 (1996)] inhibition activity. At best, only a small or no effect on the inhibitory activity of p27 was noted.

Purified cyclin E/CDK2 and cyclin A/CDK2 were used to directly examine the effects of p27 and E7 in a solution kinase assay. Similar to the above results, little or no effect of GST-E7 on p27 inhibition of CDK2 activity was noted. However, a significant effect of GST-16E7 and GST-31E7 on cyclin E/CDK2 and cyclin A/CDK2 histone H1 kinase activity was noted. PhosphorImager® analysis indicated a 26-fold increase in cyclinA/CDK2 kinase activity in the presence of GST-16E7. A smaller 1.9-fold increase in pRb kinase activity was also noted. No kinase activity was noted in any GST-E7 preparation and GST alone also had no effect. These results indicated that E7 was able to significantly and substantially alter the substrate specificity of cyclin/CDK complexes. A linear dose response was noted for the GST-E7 effect, with a 50% stimulatory concentration of E7 of approximately 0.18 μM and a peak stimulatory activity of approximately 0.29 μM. These results suggested that E7 was able to directly alter CDK2 activity and/or substrate specificity using histone H1 protein as substrate.

Results also indicated that cyclin E/CDK2 phosphorylation of purified MBP-HPV 18 E1 fusion protein was stimulated 2.3-fold by the addition of HPV 16E7. CDK2 did not phosphorylate MBP alone. The phosphorylation of E1 was completely inhibited by the addition of p27 even in the presence of excess GST-16E7. Thus, GST-E7 was able to directly promote CDK2-dependent phosphorylation of multiple substrates, including HPV18 E1. Phosphorylation of HPV E2 by CDK2/cyclinA was also enhanced by addition of E7, but E2 was a poor substrate for CDK2/cyclinE in the presence or absence of E7.

E1 phosphorylation is an important biological event because it permits amplification of the HPV genome in differentiated cells that would not normally support DNA synthesis. E1 is a 72 kDa phosphoprotein that initiates ori-dependent HPV replication [Cho, et al., Intervirology 1994;37:150–8 (1994)]. Based on amino acid sequence similarity, E1 has been grouped in the helicase superfamily III [Koonin, Nucl. Acids Res. 21:2541–7 (1993)]. Phosphorylation of E1 is important for activating HPV DNA replicating activity in vitro, suggesting that phosphorylation is important for coordinating viral and host replication machinery [Ma, et al., Proc. Natl. Acad. Sci. (USA) 96:382–7 (1999)]. E1 possesses an RXL cyclin-interaction motif which enables its efficient phosphorylation by cyclin-dependent kinases (CDKs). E1 lacking CDK phosphorylation sites binds E2 but is deficient for activating HPV replication [Ma, et al., Proc. Natl. Acad. Sci. (USA) 96:382–7 (1999)]. The phosphorylation results described above therefore suggest a mechanism by which HPV E7 might redirect CDK2 specificity to E1, and suggest a means by which E7 might preferentially promote viral DNA replication in differentiated keratinocytes.

Results also suggested that E7 can bind p21 and p27, but that E7 has little or no ability to overcome the CDK inhibitory activity of these proteins, and these results are inconsistent with previous reports. Previously published work, however, used immunoprecipitated kinase activity for studying functional aspects of E7-CDK inhibitor interaction [Funk, et al., Genes & Dev 11:2090–100 (1997); Jones, et al., Genes & Dev 11:2101–11 (1997), Zerfass, et al., Oncogene 13:2323–30 (1996)] while the present studies utilized purified kinase complex. The previous studies may have therefore overlooked any direct E7 effects on kinase activity, or misinterpreted such effects as arising from binding to the inhibitor rather than binding directly to the kinase, due to the lack of purity of these preparations.

In addition, the present results indicated that HPV-E7 derived from papillomaviruses with both high or low potential for oncogenic progression significantly activated CDK2. HPV31 and HPV16 activated CDK2 histone kinase activity by 12.6- and 18.2-fold, respectively, while the low risk-derived E7 from HPV6b activated by 15.8 fold.

Example 3

Effects of HPV E7 on Various Kinases

In an attempt to determine if the E7 effects on kinase activity were specific for members of the cyclin-dependent kinase family, various kinase/substrate combinations were examined for enhanced activity in the presence of E7.

When HPV16-E7 was added to either cyclinA/CDK2 or cyclinE/CDK2 using histoneH1 as the substrate, a large increase (26-fold and 13-fold) over controls was noted as described above. When the retinoblastoma (pRb) protein was used as a substrate for cyclinE/CDK2 a 1.9-fold increase over background was noted. The related cyclin-dependent kinase CDK5 complexed with p25 also showed an increase in H1 phosphorylation, albeit less than CDK2, with a 4.5-fold increase over controls. In other assays, it was observed that MAP kinase 1 activity and CDC2/cyclinB activity were unaffected by HPV16 E7, suggesting that E7 kinase activation is specific for members of the cyclin-dependent kinase family.

Example 4

Kinetics of Activation of CDK2 by HPV E7

Experiments were then designed to determine the effects of substrate concentration on HPV16-E7 stimulation of CDK2/cyclinA histone kinase activity using the kinase assay experimental conditions described above in Example 2 with minor modifications. Initial experiments indicated that a 15 minute assay fell within the linear range of the kinase activity, and as a result, all assays were carried out for 15 minutes. In addition, cyclinA/CDK2 complex was pre-incubated with an amount of HPV16-E7 that had been determined in previous experiments to yield the maximum activation of CDK2 kinase.

Using this approach, results permitted a non-linear least squares curve fit using the Michaelis-Menton equation to give a $K_m$ of 1.1+/−0.2 μM for histone H1, a concentration similar to the $K_m$ of 1.4 μM previously determined for histone phosphorylation by cyclinA/CDK2 [Connell-Crowley et al., *Mol. Biol. Cell* 4: 79–92, 1993]. These results therefore suggested that the large effect that HPV-E7 has upon CDK2 activity was not achieved through alteration of substrate binding, but instead through direct alteration of the CDK2 catalytic mechanism.

Example 5

Mutagenesis of E7 and Determination of Critical Amino Acid Sequences

In an attempt to identify E7 amino acids critical to CDK2 binding and/or activation, point mutations were introduced into the E7 sequence and changes in CDK2 kinase activation were determined as [follows] discussed below. In general, the structure of E7 can be divided into three regions: CR1 extends from amino acid residue 1 to approximately residue 16, CR2 includes approximately amino acids 17 to 38, and CR3 encompasses approximately residue 39 to 98. Within each of CR2 and CR3, several biologically significant regions have been identified, including, a Rb binding domain (residues 22–26) and casein kinase II phosphorylation site (residues 31–37) in CR2, and at least two zinc-binding domains in CR3. The various mutants were prepared in view of these E7 regions.

E7 Point Mutations

All site directed mutations of E7 constructs were made using a QuikChange™ kit (Stratagene). In most cases, HPV16 E7 was mutated. The following conservative amino acid changes within previously defined functional regions of the 98 amino acid protein HPV 16 E7 were introduced:

| Amino Acid Changes | E7 Functional Region |
|---|---|
| M12→L12 (Δ12) | |
| C24, E26→S24, D26 (Δ24, 26) | Rb Binding Consensus Domain (LXCXE) |
| S31, S32→G31, G32 (Δ31, 32) | Casein Kinase II Domain |
| C91→W91 (Δ91) | Putative metal-binding motif |

The PCR primers set out below were used to introduce the changes.

M12→L12 (Δ12)
Sense SEQ ID NO: 22
TACATTGCATGAATATTTGTTAGATTTGCAACCAG
Antisense SEQ ID NO: 23
CTGGTTGCAAATCTAACAAATATTCATGCAATGTA
C24,E26→S24,D26 (Δ24, 26)
Sense SEQ ID NO: 24
GAGACAACTGATCTCTACTCTTATGT-CAATTAAATGACAGC
Antisense SEQ ID NO: 25
GCTGTCATTTAATTGATCATAAGAGTA-GAGATCAGTTGTCTC
S31,S32→G31,G32 (Δ31,32)
Sense SEQ ID NO: 26
GAGCAATTAAATGACGGCGGAGAGGAG-GAGGATGAA
Antisense SEQ ID NO: 28
TTCATCCTCCTCCTCTCCGCCGTCATT-TAATTGCTC
C91→W91 (Δ91)
Sense SEQ ID NO: 27
ACACTAGGAATTGTGGGCCCCATCTGTTCTCAG
Antisense SEQ ID NO: 29
CTGAGAACAGATGGGGCCCACAATTCCTAGTGT Multiple mutations within the E7 coding sequence were generated by a series of site-directed mutagenesis reactions. At each step, the mutagenesis was confirmed by sequence analysis. The isolated mutant proteins were examined for relative ability to activate CDK2 under conditions described above. Results are set out in Table 1 below.

TABLE 1

Amino Acid Changes versus CDK2 Activation

| Amino Acid Changes | % Control Activation | |
|---|---|---|
| | Exp. 1 | Exp. 2 |
| Δ12 | 96.7 | |
| Δ24, 26 | 86.7 | 81.3 |
| Δ31, 32 | 77.1 | |
| Δ91 | 81.7 | 78.7 |
| Δ12; Δ24, 26 | 85.2 | 93.5 |
| Δ24, 26; Δ31, 32 | 88.2 | 95.6 |
| Δ24, 26; Δ91 | 69.4 | 86.4 |
| Δ12; Δ24, 26; Δ31, 32 | | 83.1 |
| Δ24, 26; Δ31, 32; Δ91 | | 70.6 |

Results indicated that E7 can tolerate multiple alterations in amino acid sequence within previously determined functional domains and still activate CDK2 kinase activity. This conclusion is demonstrated by E7 proteins having up to five mutated residues showing little change in the ability to activate CDK2.

E7 Truncation Mutants

In an attempt to more fully elucidate E7 regions required for CDK2 activation, E7 fragments were tested in the above assay. HPV16-E7 truncations were expressed using DNA wherein stop codons were introduced after residues 87, 69, 48, 38, 27, and 15 in the full length coding E7 sequence. The GST-HPV16 E7 pGEX-4T-3 expression construct was modified using site-directed mutagenesis with a Quick-Change™ kit (Stratagene) and the proper sequence alterations were confirmed by sequence using a Perkin-Elmer ABI-PRISM®. The truncated E7-GST fusion proteins were purified and tested as described above. Primers used for to introduce stop codons in the E7 coding region are set out below.

GST-16E7(1–15)
Sense SEQ ID NO: 40
GCATGAATATATGTTAGATTTGTAACCA-GAGACAACTGATCTC
Antisense SEQ ID NO: 41
GAGATCAGTTGTCTCTGGTTA-CAAATCTAACATATATTCATGC
GST-16E7(1–27)
Sense SEQ ID NO: 30
CTACTGTTATGAGCAATAAAATGACAGCTCAGAG
Antisense SEQ ID NO: 31
CTCTGAGCTGTCATTTTATTGCTCATAACAGTAG
GST-16E7(1–38)

Sense SEQ ID NO: 42
CAGAGGAGGAGGATGAAATATAAGGTC-CAGCTGGACAAGCAG
Antisense SEQ ID NO: 43
CTGCTTGTCCAGCTGGACCT-TATATTTCATCCTCCTCCTCTG
GST-16E7(1–48)
Sense SEQ ID NO: 32
GACAAGCAGAACCGGACTGAGCCCATTA-CAATATTG
Antisense SEQ ID NO: 33
CAATATTGTAATGGGCTCAGTCCGGT-TCTGCTTGTC
GST-16E7(1–69)
Sense SEQ ID NO: 34
GCTTCGGTTGTGCGTATAAAGCACACACGTAGAC
Antisense SEQ ID NO: 35
GTCTACGTGTGTGCTTTATACGCACAACCGAAGC
GST-16E7(1–87)
Sense SEQ ID NO: 36
GTTAATGGGCACACTATGAATTGTGTGCCCCATC
Antisense SEQ ID NO: 37
GATGGGGCACACAATTCATAGTGTGCCCATTAAC Results indicated that deletion of HPV16 E7 residues between 48 and 98 from the carboxy terminus caused a slight decrease in CDK2 activation capability. HPV E7(1–87), HPV E7(1–69), and HPV E7(1–48) all showed similar degrees of activation of CDK2, with relative kinase activity of 76.67%, 82.45%, and 73.25%, respectively, compared to activity in the presence of full length E7. HPV E7(1–38) also demonstrated relative kinase activity of approximately 72%. Truncation of residues 28–48 resulted in a significant drop in CDK2 activation, to 28.64% in one experiment and to 52% in a repeat experiment of that of full length E7, suggesting that the majority of the CDK2 activation function of E7 resides in the amino-terminal portion of the protein. HPV E7(1–15), however, exhibited only 15% relative kinase active, indicating that the majority of the CDK2 promoting activity arises from sequences found in both CR1 and CR2 E7 regions. These results were confirmed by truncation of the HPV16 E7 amino-terminus using the following PCR strategy.

The pGEX-4T-3 GST-HPV16 E7 expression vector was also used as template to prepare amino terminal E7 deletion mutants. Residues 1–39 of HPV16 E7 were eliminated using (i) a reverse PCR primer that hybridized to the antisense strand immediately 5' of the E7 gene in the pGEX-4T-3 vector, and (ii) a forward second primer which hybridized starting at codon 39 (and downstream from codon 39) of the E7 gene. PCR conditions were identical to those used for carboxy terminal site-directed mutagenesis. The reaction resulted in the entire vector and E7 gene being amplified with the exception of that region of E7 encoding amino acid residues 1–38. The primers used were as follows.

GST-16E7(39–98) primers
Sense GATGGTCCAGCTGGACAAGC SEQ ID NO: 38
Antisense CATGGATCCACGCGGAACCAG SEQ ID NO: 39

The resulting PCR products were digested with DpnI to eliminate template DNA, extracted with phenol-chloroform, ethanol precipitated, and transformed into *E. Coli* strain JM 109. Isolated clones were prepared and the proper construct, missing the 5'-region of the E7 gene encoding residues 1–38, was confirmed by restriction endonuclease digestion and sequence analysis. Expression of the GST-HPV16-E7 (39–98) polypeptide was induced and the truncated protein was isolated using glutathione affinity chromatography. Proper size was determined using SDS-PAGE. Similarly GST-E7 constructs were generated encoding HPV16 amino acids 9–98 and 16–98.

GST-HPV16-E7(39–98) assayed for the ability to activate cyclinA/CDK2 showed 28.6% of the activation activity of full length GST-HPV 16 E7. In a repeat experiment, GST-HPV16-E7(39–98) showed 18% activation potential. GST-HPV16-E7(9–98), however, showed 64% activation of full length E7, and GST-HPV16-E7(16–98) showed 53% activation. These results, together with earlier results using the carboxy-terminal truncation mutants, indicates that smaller regions within E7, particularly within the amino-terminal portion of the protein, are critical for activation of cyclin-dependent kinases.

In view of these results, additional constructs were prepared encoding only internal amino acid regions of E7 or deletion mutants wherein internal E7 sequences were removed. Construct GST-16E7 (16–38) was prepared by introducing a stop codon in the construct encoding GST-16E7(16–98), while constructs GST-16E7(39–98) and GST-E7 (20–48) were prepared using a QuikChange™ mutagenesis kit using PCR primers to exclude amino terminal sequence using pGEX16E7 and pGEX16E7(1–48) as template DNA. Constructs bearing internal E7 amino Δ9-13, 13-15, Δ34-37, Δ21-37, Δ31-37, or Δ16-37 were deleted using the QuikChange™ mutagenesis kit according to the manufacturer's suggested protocol and pGEX-16E7 DNA as template.

Results from kinase assays using constructs GST-16E7 (16–38), GST-16E7(39–98), and GST-E7 (20–48) showed these E7 residues were able to induce kinase activity to levels 53%, 18%, and 33%, respectively, of that by full length E7. Inducing activity for the various internal deletion mutants is shown in Table 2.

TABLE 2

Amino Acid Changes versus CDK2 Activation

| Amino Acid Changes | % Control Activation |
| --- | --- |
| Δ9–13 | 90 |
| Δ13–15 | 76 |
| Δ34–37 | 80 |
| Δ9–13, Δ34–37 | 72 |
| Δ22–26 | 85 |
| Δ31–37 | 80 |
| Δ22–26, Δ31–37 | 72 |

Combined, these result indicate that inactivation of the Rb-binding domain, the casein kinase II domain or the zinc-binding domains results in only a small decrease in the ability of E7 to activate CDK2 kinase activity. Similarly, deletion of both the Rb-binding and casein kinase II domains resulted in a loss of only 28% of that determined for full length E7, and none of the internal deletions from the CR1 and CR2 regions, alone or in combination, significantly affected activation by E7.

The E7 CR1 and CR2 regions show high degrees of similarity to non-contiguous portions of adenovirus E1A protein and SV40 T antigen. In view of this degree of similarity, it is expected that activation of CDK2 is also a biological property of these and other viral proteins.

Example 6

E7 Interaction with CyclinA

In order to characterize E7 binding to the CDK2/cyclin complex, binding assays were carried out using CDK2 and cyclinA individually.

HighFive™ cells (Invitrogen) were infected with baculovirus expressing GST-cyclinA (described above) or hemagglutinin (HA)-tagged CDK2 [Desai, et al., *Mol. Cell. Biol.* 3:571–582 (1992)]. GST-cyclinA-expressing cells were lysed ($4 \times 10^7$ cells/ml) in lysis buffer (20 mM Tris-HCl, pH 8.0, 2 mM EDTA, 100 mM NaCl, 5 mM NaF, 1 mM $Na_3VO_4$, 0.5% NP-40, 10 μg/ml leupeptin, 4 μg/ml aprotinin, and 1 mM PMSF) and insoluble material removed with centrifugation. GST-cyclinA expression was verified by SDS-PAGE and immmunoblotting. HA-CDK2-expressing cells were lysed in low salt, hypotonic lysis buffer [10 mM HEPES, pH 7.4, 10 mM NaCl, 1 mM EDTA, 0.1% NP-40, 1 mM DTT, 20 μM 4-(2-aminoethyl)benzenesulfonyl fluoride (AEBSF) and 1× Complete™ proteinase inhibitor cocktail (Boehringer Mannheim)].

Glutathione agarose beads (25 μl) (Sigma) were preincubated with 4% bovine serum albumin (BSA) in PBS, washed 3× in 1 ml lysis buffer, added to 1 ml GST-cyclinA lysate, and incubated at 4° C. for 1 hr with mixing. The beads were washed 4× with 1 ml lysis buffer, 2× with 1 ml binding buffer (20 mM HEPES, pH 7.4, 10 mM KCl, 100 mM NaCl, 1 mM EDTA, 1 mM EGTA, 0.1% NP-40, 12.5% glycerol, 1 mM DTT, and 1× Complete™ proteinase inhibitor cocktail) containing 100 mM NaCl, and resuspended in 0.4 ml binding buffer. Purified HPV16E7 (4 μg) was added to the beads and incubation was carried out for 1.5 hr at 4° C. with agitation. The beads were washed 5× with 1 ml binding buffer, boiled in 2× Laemmli buffer, and analyzed using SDS-PAGE and immunoblotting.

Crude HA-CDK2 lysate (0.2 ml) was diluted 1:5 in hypotonic lysis buffer containing 150 mM NaCl and precleared with 1 μg mouse IgG and 25 μl Protein A/Protein G PLUS-Agarose (Santa Cruz Biotechnology, Inc.) for 1 hr at 4° C. Immunoprecipitation of HA-CDK2 was carried out with 1 μg anti-HA monoclonal antibody 12CA2 (Roche Molecular Biochemicals) and 20 μl Protein A/Protein G PLUS-Agarose for 1 hr at 4° C. The beads were washed 3× with 1 ml hypotonic lysis buffer containing 150 mM NaCl, 2× with 1 ml binding buffer, and resuspended in 0.4 ml binding buffer. Purified HPV16E7 (4 μg) was added to the beads and incubation was carried out at 4° C. for 1.5 hr. The beads were washed in 5× with 1 ml binding buffer, blotted in 2× Laemmli sample buffer, and analyzed by SDS-PAGE and immunoblotting.

Results showed E7 binding to beads containing GST-cyclinA, but no binding to beads with immobilized HA-CDK2. These results suggest that the action of E7 on CDK2 enhanced kinase activity may be effected through binding interactions with the cyclin component in the CDK2/cyclin complex. This binding interaction is consistent with the theory that E7 is able to alter CDK2 substrate specificity in view of the fact that cyclins play a role in mediating CDK2 substrate specificity [Roberts, Cell 98:129–132 (1999)]. In one mode of action, E7 binding may redirect CDK2 to viral substrates which participate in viral DNA replication. Alternatively, E7 binding can alter CDK2 specificity for cellular substrates which either participate in promoting the onset of host cell S phase or redirect cellular substrates to participate in replicating viral DNA.

Numerous modifications and variations in the invention as set forth in the above illustrative examples are expected to occur to those skilled in the art. Consequently only such limitations as appear in the appended claims should be placed on the invention.

What is claimed is:

1. A method for identifying an inhibitor of E7-induced CDK2 kinase activity, comprising the steps of
   a) measuring CDK2 kinase activity on a CDK2 substrate in the presence of human papillomavirus (HPV) E7, or a CDK2 complex-binding fragment thereof, and in the presence and absence of a test compound, and
   b) identifying the test compound as an inhibitor of E7-induced CDK2 kinase activity when decreased phosphorylation of the CDK2 substrate is detected in the presence of the test compound compared to phosphorylation of the CDK2 substrate detected in the absence of the test compound.

2. The method according to claim 1 wherein the HPV E7 fragment is selected from the group consisting of amino acid residues 1 to 27, amino acid residues 1 to 38, amino acid residues 1 to 48, amino acid residues 1 to 69, and amino acid residues 1 to 87 of SEQ ID NO: 1.

3. A method far identifying an inhibitor of E7-induced CDK2 kinase activity comprising the steps of
   a) measuring CDK2 kinase phosphorylation of a CDK2 substrate;
   b) measuring increased CDK2 kinase phosphorylation of the CDK2 substrate in the presence of human papillomavirus (HPV) E7, or a CDK2 complex-binding fragment thereof, to determine E7-induced CDK2 kinase activity;
   c) measuring CDK2 kinase phosphorylation of the CDK2 substrate in the presence of HPV E7, or a CDK2 complex-binding fragment thereof, and in the presence of a test inhibitor compound; and
   d) identifying the teal compound as an inhibitor of E7-induced CDK2 kinase activity when the increased phosphorylation measured in step (b) is reduced in the presence of the test compound.

4. The method according to claim 3 wherein the HPV E7 fragment is selected from the group consisting of amino acid residues 1 to 27, amino acid residues 1 to 38, amino acid residues 1 to 48, amino acid residues 1 to 69, and amino acid residues 1 to 87 as set out in SEQ ID NO: 1.

5. The method according to one of claims 1, 2, 3, or 4 wherein the CDK2 substrate is selected from the group consisting of histone H1, HPV protein E1 and HPV protein E2.

6. The method of claim 5 wherein measuring of CDK2 kinase activity is carried out in the presence of a cyclin.

7. The method of claim 5 wherein the cyclin is selected from the group consising of cyclinA and cyclinE.

8. A method for identifying an anti-viral agent comprising the steps of
   a) identifying an inhibitor of E7-induced increase in CDK2 kinase activity;
   b) measuring viral proliferation in the presence and absence of the inhibitor identified in (a); and
   c) identifying the inhibitor as an antiviral agent when decreased viral proliferation is detected in the presence of the inhibitor compared to viral proliferation in the absence of the inhibitor.

* * * * *

UNITED STATES PATENT AND TRADEMARK OFFICE
CERTIFICATE OF CORRECTION

PATENT NO.   : 6,641,994 B2
DATED        : November 4, 2003
INVENTOR(S)  : Christopher Fisher et al.

It is certified that error appears in the above-identified patent and that said Letters Patent is hereby corrected as shown below:

Column 35,
Line 43, cancel "far" and insert -- for --.

Column 36,
Line 26, cancel "teal" and insert -- test --.

Signed and Sealed this

Twelfth Day of October, 2004

JON W. DUDAS
*Director of the United States Patent and Trademark Office*

SEQUENCE LISTING

<160> NUMBER OF SEQ ID NOS: 43

<210> SEQ ID NO 1
<211> LENGTH: 98
<212> TYPE: PRT
<213> ORGANISM: Papillomavirus sylvilagi

<400> SEQUENCE: 1

Met His Gly Asp Thr Pro Thr Leu His Glu Tyr Met Leu Asp Leu Gln
 1               5                  10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 2
<211> LENGTH: 28
<212> TYPE: DNA
<213> ORGANISM: Artificial Sequence

```
<220> FEATURE:
<223> OTHER INFORMATION: Description of Artificial Sequence: primer

<400> SEQUENCE: 2
cgggatccat gcgtggagaa acacctac                                          28

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 3
cgggatcctt acagtctagt agaacag                                           27

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 4
cgggatccat gcatggaaga catgtt                                            26

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 5
ccgctcgagt taggtcttcg gtgcgc                                            26

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 6
cgggatccat gcatggagat acacctac                                          28

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 7
ccgctcgagt tatggtttct gagaacagat g                                      31

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 8
gcctcgagat gtcagaaccg gctggggatg                                        30
```

```
<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 9
gcggatcctt agaaggtaga gcttgggcag                                          30

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 10
gcctcgagct gcccaagctc taccttc                                             27

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 11
cggatcctat gtcaaacgtg cgagtg                                              26

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 12
gcggatcctt agggcttcct cttggag                                             27

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 13
aggatcctta cgtttgacgt cttctg                                              26

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 14
gcctcgagat gtcaaacgtg cgagtgtc                                            28

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: primer
```

<400> SEQUENCE: 15
gcggatcctt acaccttgca ggcacctttg          30

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 16
gcctcgagaa aggtgcctgc aaggtgc          27

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 17
gcggatcctt acgtttgacg tctctg          26

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 18
gatcagatct catgaaggag gacggcggcg          30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 19
gcagatcttc agtggtggtg gtggtggtgg          30

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 20
gggcggccgc atgtcccta tactaggtta t          31

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 21
gggcggccgc gtcagtcagt cacgatg          27

<210> SEQ ID NO 22

<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 22
tacattgcat gaatatttgt tagatttgca accag                          35

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 23
ctggttgcaa atctaacaaa tattcatgca atgta                          35

<210> SEQ ID NO 24
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 24
gagacaactg atctctactc ttatgtcaat taaatgacag c                   41

<210> SEQ ID NO 25
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 25
gctgtcattt aattgatcat aagagtagag atcagttgtc tc                  42

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 26
gagcaattaa atgacggcgg agaggaggag gatgaa                         36

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 27
acactaggaa ttgtgggccc catctgttct cag                            33

<210> SEQ ID NO 28
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 28
ttcatcctcc tcctctccgc cgtcatttaa ttgctc                36

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 29
ctgagaacag atggggccca caattcctag tgt                33

<210> SEQ ID NO 30
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 30
ctactgttat gagcaataaa atgacagctc agag                34

<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 31
ctctgagctg tcattttatt gctcataaca gtag                34

<210> SEQ ID NO 32
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 32
gacaagcaga accggactga gcccattaca atattg                36

<210> SEQ ID NO 33
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 33
caatattgta atgggctcag tccggttctg cttgtc                36

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 34
gcttcggttg tgcgtataaa gcacacacgt agac                34

<210> SEQ ID NO 35
<211> LENGTH: 34
<212> TYPE: DNA

```
<213> ORGANISM: Artificial Sequence
<220> FEATURE:
<223> OTHER INFORMATION: Description of Artificial Sequence: primer

<400> SEQUENCE: 35
gtctacgtgt gtgctttata cgcacaaccg aagc                                34

<210> SEQ ID NO 36
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 36
gttaatgggc acactatgaa ttgtgtgccc catc                                34

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 37
gatggggcac acaattcata gtgtgcccat taac                                34

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 38
gatggtccag ctggacaagc                                                20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 39
catggatcca cgcggaacca g                                              21

<210> SEQ ID NO 40
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 40
gcatgaatat atgttagatt tgtaaccaga gacaactgat ctc                      43

<210> SEQ ID NO 41
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 41
gagatcagtt gtctctggtt acaaatctaa catatattca tgc                      43
```

```
<210> SEQ ID NO 42
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 42
cagaggagga ggatgaaata taaggtccag ctggacaagc ag                    42

<210> SEQ ID NO 43
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 43
ctgcttgtcc agctggacct tatatttcat cctcctcctc tg                    42
```